United States Patent
Rose (10) Patent No.: US 10,449,132 B2
(45) Date of Patent: *Oct. 22, 2019

(54) PROCESS FOR TREATING HAIR

(71) Applicant: Kao Corporation, Tokyo (JP)

(72) Inventor: Burkhard Rose, Darmstadt (DE)

(73) Assignee: KAO CORPORATION, Tokyo (JP)

(*) Notice: Subject to any disclaimer, the term of this patent is extended or adjusted under 35 U.S.C. 154(b) by 267 days.

This patent is subject to a terminal disclaimer.

(21) Appl. No.: 15/022,144

(22) PCT Filed: Sep. 16, 2013

(86) PCT No.: PCT/EP2013/069134
§ 371 (c)(1),
(2) Date: Mar. 15, 2016

(87) PCT Pub. No.: WO2015/036051
PCT Pub. Date: Mar. 19, 2015

(65) Prior Publication Data
US 2016/0228342 A1    Aug. 11, 2016

(51) Int. Cl.
*A61Q 5/02* (2006.01)
*A61Q 5/12* (2006.01)
*A61K 8/365* (2006.01)
*A61K 8/46* (2006.01)

(52) U.S. Cl.
CPC .............. *A61K 8/365* (2013.01); *A61K 8/463* (2013.01); *A61Q 5/02* (2013.01); *A61Q 5/12* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| 5,609,168 A | 3/1997 | Kischka et al. |
| 2006/0269495 A1* | 11/2006 | Popp ...................... A61K 8/365 424/70.1 |
| 2007/0202067 A1* | 8/2007 | Kolly-Hernandez ....................... A61K 8/585 424/70.11 |
| 2008/0131392 A1* | 6/2008 | Hoffmann ................ A61K 8/85 424/70.11 |
| 2013/0189213 A1* | 7/2013 | Ivanova ................... A61K 8/31 424/70.27 |

FOREIGN PATENT DOCUMENTS

| EP | 0 070 074 A2 | 1/1983 |
| EP | 0 358 216 A2 | 3/1990 |
| EP | 1923043 * | 5/2008 |
| EP | 2 258 337 A1 | 12/2010 |
| GB | 1 416 564 | 12/1975 |
| JP | 2005-194261 A | 7/2005 |
| JP | 2007-176826 A | 7/2007 |
| JP | 2008-208071 A | 9/2008 |
| WO | WO-2011/104282 A2 | 9/2011 |
| WO | WO-2011/104282 A3 | 9/2011 |
| WO | WO-2012/010351 A2 | 1/2012 |
| WO | WO-2012/105985 A1 | 8/2012 |
| WO | WO-2013/092959 A1 | 6/2013 |
| WO | WO-2014/016658 A1 | 1/2014 |
| WO | WO-2014/068101 A2 | 5/2014 |
| WO | WO-2014/068102 A2 | 5/2014 |

OTHER PUBLICATIONS

XP-002703715A, MINTEL document titled Moroccan Relaxing Treatment with Argan Oil http://www.gnpd.com, Jan. 2012, Brazil.

* cited by examiner

*Primary Examiner* — Jyothsna A Venkat
(74) *Attorney, Agent, or Firm* — Foley & Lardner LLP (57) ABSTRACT

The present invention relates to a process for reducing the frizziness and improving the manageability of the hair, wherein the hair is treated with a cleansing composition and/or a conditioning composition comprising at least one carboxylic acid of the formula (I): R—CO—COOH and/or a hydrate thereof and/or a salt thereof.

8 Claims, 1 Drawing Sheet

PROCESS FOR TREATING HAIR

FIELD OF THE INVENTION

The present invention relates to a method for reducing the frizziness and improving the manageability of frizzy hair and a kit for the method.

BACKGROUND OF THE INVENTION

A known method for straightening curly or frizzy hair involves the use of straightening irons. The high temperature of the iron leads to a breakage of hydrogen bonds in the keratin of the hair, achieving a temporary straightening. The hydrogen bonds are formed again by the action of moisture, so that the hair reverts back to its original shape over the time because of air humidity, and the straightening effect vanishes after washing the hair.

The shape of the hair is largely determined by the disulfide bonds linking two cysteine moieties of the hair keratin. In order to achieve a more permanent shaping of the hair, known methods involve the cleavage of the disulfide bonds by the action of a sulfide- or thio group containing reducing agent. After the hair has been brought into the desired shape, new disulfide bonds are formed by applying an oxidizing agent such as hydrogen peroxide, thus fixing the shape of the hair. The use of such agents, however, may cause damage to the hair.

As an example for this kind of hair shaping treatment, reference is made to GB 1 416 564, describing reducing compositions comprising thioglycolates or thiolactates as reducing agents and fixing compositions comprising hydrogen peroxide as an oxidizing agent. The reducing compositions may further comprise a salt of glyoxylic acid as a buffering agent.

As an alternative to the above-described two-step reduction and oxidation process, the disulfide bridges can be cleaved by the action of an alkaline agent such as sodium hydroxide at a pH of about 11 or higher. Under these conditions, the disulfide (or cystin) moiety can undergo a disproportionation reaction under the elimination of sulfur, and is cleaved into an alpha-beta-unsaturated dehydro-alanine moiety and a cysteine moiety. After the hair has been brought into the desired shape, the dehydro-alanin moieties and the cysteine moieties form thioether bonds and combine to lanthionine, stabilizing the straightened state of the hair. Since the disulfide or cystin moieties are converted into lanthionine moieties, this type of hair straightening process using an alkaline agent is also called lanthionization.

Both the two-stage reduction/oxidation method and the lanthionization method rely on a cleavage of the disulfide bonds and the formation of new bonds among the hair proteins, leading to an irreversible change of the shape of the hair. This means that these processes can achieve a permanent straightening, wherein the treated portion of the hair maintains its shape, and the straightening effect only vanishes because of the growth of the hair.

Recently, it has been found that α-keto acids such as glyoxylic acid, which are known as a buffering agent in cosmetic compositions, may have a semi-permanent straightening effect when used in combination with mechanical straightening means.

In this respect, WO 2011/104282 describes a process for semi-permanent hair straightening, which involves applying a composition comprising an α-keto acid onto the hair, leaving the composition in contact with the hair for 15 to 120 minutes, drying the hair and straightening the hair with a straightening iron at a temperature of 200±50° C.

Furthermore, WO 2012/010351 describes a treatment for semi-permanent straightening of curly, frizzy or wavy hair by applying a solution of glyoxylic acid in combination with mechanical straightening, using a straightening iron at a temperature of 200±30° C. After the treatment, the hair is said to retain its shape for at least six consecutive washings.

EP 0685 219 describes a composition useful as a pre-treatment agent before subjecting the hair to a perm wave treatment, the composition comprising a film-forming cationic, anionic and/or amphoteric polymer, an amphoteric surfactant, an organic acid and a C2 to C4 alcohol, and being free of cationic surfactants.

SUMMARY OF THE INVENTION

The present invention provides a method for reducing the frizziness and improving the manageability of hair, comprising the treatment of the hair with one or both of:
a hair cleansing composition (shampoo) having a pH of 4 or lower and comprising one or more surfactants selected from anionic, non-ionic and amphoteric surfactants and at least one carboxylic acid of the Formula (I) and/or a hydrate thereof and/or a salt thereof; and
a hair conditioning composition (conditioner) having a pH of 4 or lower and comprising one or more conditioning components and at least one carboxylic acid of the Formula (I) and/or a hydrate thereof and/or a salt thereof:

R—CO—COOH            Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

Another aspect of the present invention concerns the use of one or both of the above-described hair cleansing composition and the hair conditioning composition for reducing the frizziness and improving the manageability of the hair, and to a kit comprising the cleansing composition and the conditioning composition.

In a preferred embodiment, the cleansing composition comprises an anionic surfactant and the conditioning composition comprises a cationic surfactant.

DETAILED DESCRIPTION OF THE INVENTION

The above-described prior art methods using a compound such as glyoxylic acid in combination with straightening irons achieve a semi-permanent straightening of the hair. These methods are time-consuming and generally need to be performed by a professional hair dresser.

Thus, there also is demand for less time-consuming hair straightening methods, which do not require a salon visit and can be performed by the consumers themselves, but still lead to a substantial frizz reduction and manageability improvement of frizzy or wavy hair.

The present inventors surprisingly found that this demand can be satisfied by a method involving the treatment of the hair with a specific cleansing composition and/or a specific conditioning composition comprising at least one carboxylic acid of the Formula (I). This method does not require the use of specific equipment such as hair straightening irons, and can be easily integrated into the consumers' everyday hair care measures.

As a result, the present invention provides a convenient process for reducing the frizz and improving the manageability of the hair without requiring the time-consuming and expensive services of a professional hair dresser. Besides, the process of the present invention is generally milder than the treatment with a straightening iron at high temperature, so that the risk of hair damage can be reduced.

For increasing the frizz reducing and manageability improving effect, the treatment with the cleansing composition and/or the conditioning composition is preferably carried out repeatedly. Carrying out the treatment repeatedly means that the treatment is carried out more than once. Typically, the treatment is carried out at least once a week, preferably at least twice a week, more preferably at least three times a week, yet more preferably every day.

1. The Carboxylic Acid of Formula (I)

The cleansing composition and the conditioning composition comprise at least one carboxylic acid of the following formula (I) as the active component:

Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_8$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

As preferred examples, glyoxylic acid, pyruvic acid and 2-ketobutyric acid can be mentioned.

The carboxylic acid of Formula (I) may be comprised in the composition in its free acid form. The carbonyl group adjacent to the acid group of the acid may also be present in the hydrate form. Apart from the free acid form and the hydrate thereof, salts of the acid or the hydrate may also be used.

The hydrate of the acid of Formula (I) may be formed when providing the composition as an aqueous solution. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, and alkaline earth metal salts such as the magnesium salt or the calcium salt may be mentioned.

In the present invention, glyoxylic acid or a hydrate thereof is the most preferred carboxylic acid of Formula (I).

2. The Cleansing Composition (Shampoo)

There are no particular limitations with respect to the cleansing composition (shampoo) used in the present invention, as long as it comprises at least one carboxylic acid of the Formula (I) defined above and/or a hydrate thereof and/or a salt thereof. Preferably, the cleansing composition comprises glyoxylic acid or a hydrate thereof.

The concentration of the at least one compound of Formula (I) in the cleansing composition is preferably in the range of 0.01 to 5%, more preferably 0.1 to 5%, more preferably 0.2 to 5%, even more preferably 0.2 to 4%, yet more preferably 0.2 to 3% and still more preferably 0.25 to 2.5% by weight, based on the weight of the cleansing composition. Generally, a content of the compound of 0.2% or more is preferable in view of the frizz reducing effect.

For providing the cleansing effect, the cleansing composition comprises one or more surfactants selected from anionic, non-ionic and amphoteric surfactants, typically at a concentration in the range of 5 to 50% by weight, based on the weight of the total composition. Preferably, the total surfactant concentration in the cleansing composition is in the range of 7.5 to 30%, more preferably 10 to 25% by weight, based on the weight of the cleansing composition.

Preferably, the cleansing composition of the present invention comprises at least one anionic surfactant, preferably of an alkyl ether sulphate type. It is even more preferable that the cleansing composition of the present invention also comprises at least one nonionic surfactant and optionally at least one amphoteric surfactant in addition to the anionic surfactant.

In a further preferred embodiment, the cleansing composition comprises at least one anionic surfactant, preferably of the alkyl ether sulphate type, at least one non-ionic surfactant, preferably an alkyl polyglucoside and at least one amphoteric surfactant, preferably of the alkyl amido alkyl betaine type. More preferably, the composition additionally comprises an acyl amino carboxylic acid surfactant, preferably sodium lauroyl glutamate, further to the anionic, the non-ionic and the amphoteric surfactant.

In order to improve the feel of use, the cleansing composition of the present invention may preferably also comprise one or more conditioning agents, preferably selected from cationic polymers and silicone compounds as defined below in connection with the conditioner.

When adding one or more conditioning agents, the concentration thereof may suitably be in the range of 0.1 to 20% by weight, preferably 0.2 to 10% by weight, more preferably 0.5 to 5% by weight, based on the weight of the cleansing composition.

In view of the frizz reducing effect, the pH value of the cleansing composition is 4 or lower. For avoiding the risk of skin irritation and improving the safety of use as well as storage stability, it is preferable that the pH is higher than 1.5. Therefore, the pH value preferably is in the range of 1.5 to 4.0, more preferably 2 to 3.5 and even more preferably 2.5 to 3.0.

Besides, the cleansing composition may comprise further ingredients conventionally used in the field of cosmetics, such as preservatives, chelating agents, stabilizers, oxidation inhibitors, plant extracts, ultraviolet absorbers, vitamins, dyes, and fragrances.

Anionic Surfactants

Preferably, the cleansing composition comprises one or more anionic surfactants suitably in a concentration from 1 to about 30%, preferably 2 to 20%, more preferably 2 to 15%, and even more preferably 3 to 10% by weight of the cleansing composition.

There are no particular limitations as to the type of the anionic surfactant. Respective examples include anionic surfactants of the sulphate, sulphonate, carboxylate and alkyl phosphate type.

As examples for sulphate type anionic surfactants, $C_{10}$-$C_{18}$-alkyl sulfates and alkyl ether sulphates can be mentioned. Preferable examples for anionic surfactants are those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

As regards the alkyl phosphate type anionic surfactants, the salts of long-chain mono- and dialkyl phosphates, which constitute mild, skin-compatible detergents, may preferably be used.

Further anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate to are alkyl polyether carboxylic acids and the salts thereof of the formula wherein $R_1$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula wherein $R_1$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isothionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

The most preferred anionic surfactants within the meaning of the present invention are alkyl ether sulphates such as lauryl ether sulphate and aminocarboxylic acids such as lauroyl glutamate sodium salt.

Nonionic Surfactants

Preferably, the cleansing composition comprises one or more non-ionic surfactants, suitably at a concentration of 1 to 15%, preferably 2 to 10% by weight, based on the weight of the cleansing composition.

Preferable non-ionic surfactants are alkyl polyglucosides of the general formula wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components may be present, for example, long-chain fatty acid dialkanolamides, such as coco fatty acid diethanolamide and myristic fatty acid diethanolamide, which can also be used as foam enhancers.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl)amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the cleansing composition according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16".

The average degree of ethoxylation is generally between 2.5 and 25, preferably between 10 and 20.

The most preferred non-ionic surfactants are alkyl polyglucosides such as decyl, cocoyl polyglucoside and ethoxylated fatty alcohols such as laureth-16.

Amphoteric/Zwitterionic Surfactants

As further surfactant component, the cleansing composition according to the invention can also contain amphoteric or zwitterionic surfactants, for example in a concentration from about 1% to about 15%, preferably from about 2% to about 10%, by weight, based on the weight of the total composition.

It has been found out that the addition of zwitterionic or amphoteric surfactants enhances foam feeling in terms of creaminess, foam volume and as well as skin compatibility is improved.

For achieving milder formulations, the cleansing composition preferably contains an anionic surfactant (preferably of the sulphate type) in combination with an amphoteric surfactant at a weight ratio in the range of 10:1 to 1:1, preferably 5:1 to 1:1.

As the amphoteric surfactants, known betaines such as alkyl betaines, fatty acid amidoalkyl betaines and sulfobetaines, for example, lauryl hydroxysulfobetaine may be used. Long-chain alkyl amino acids, such as cocoaminoacetate, cocoaminopropionate and sodium cocoamphopropionate and acetate have also proven suitable.

In detail, it is possible to use betaines of the structure wherein $R_4$ is a $C_8$-$C_{18}$-alkyl group and n is 1 to 3; sulfobetaines of the structure wherein $R_4$ and n are same as above; and amidoalkyl betaines of the structure wherein $R_4$ and n are same as above.

The most preferred amphoteric surfactants are alkyl betaines such as lauryl betaine or cocoyl betaine and alkyl amido betaines such as cocamidopropyl betaine.

3. The Conditioning Composition (Conditioner)

There are no particular limitations with respect to the conditioning composition (conditioner) used in the present invention, as long as it comprises at least one compound according to the above general Formula (I) and/or a hydrate thereof and/or a salt thereof. Glyoxylic acid or a hydrate thereof is preferable. The conditioner preferably comprises the compound of the above Formula (I) at a concentration in the range of 0.01 to 5%, more preferably 0.1 to 5%, more preferably 0.2 to 5%, even more preferably 0.2 to 4%, yet more preferably 0.2 to 3% and still more preferably 0.25 to 2.5% by weight, based on the weight of the composition. Generally, a content of the compound of 0.2% or more is preferable in view of the frizz reducing effect The conditioning composition may be a leave-in composition, which is not rinsed off from the hair after application onto either wet or dry hair. Alternatively, the conditioner may be a rinse-off conditioner which is rinsed off from the hair after application and leaving on the hair for a certain period of time. Leave-in type conditioners are preferable in view of the frizz reducing and manageability improving performance.

Regardless of the type of application, the conditioner may be in the form of a solution, dispersion, emulsion, foam or gel. These compositions may be applied onto the hair simply by hand after rubbing into the hands and distributing them onto the hair homogeneously or by spraying onto hair either from a mechanical device or from a pressurized aerosol container.

In addition to the compound of Formula (I), the conditioner comprises one or more conditioning components. Examples of the conditioning component generally include cationic polymers, silicones, higher alcohols, organic conditioning oils (for example, hydrocarbon oil, polyolefin and fatty acid ester) and cationic surfactants. It is possible to use only a single type of conditioning component, or two or more in combination. The conditioning components adhere to the hair and improve the feel and the manageability.

Typically, the conditioner of the present invention comprises at least one conditioning component selected from cationic polymers, silicone compounds and cationic surfactants. In addition, the conditioner preferably comprises at least one oil component and/or a fatty alcohol as further conditioning components.

The concentration of the conditioning components is generally in the range of 0.1 to 90% by weight, based on the weight of the total composition. Preferably, the content of the conditioning components is in the range of 0.2 to 30 wt. %, more preferably 0.5 to 20 wt. %, based on the weight of the conditioning composition.

The conditioner of the present invention is preferably an aqueous composition and comprises at least 10% by weight of water, based on the weight of the total composition.

In view of the frizz reducing effect, the pH value of the conditioning composition is 4 or lower. For avoiding the risk of skin irritation and improving the safety of use as well as storage stability, it is preferable that the pH is higher than 1.5. Therefore, the pH value preferably is in the range of 1.5 to 4, more preferably 2 to 3.5 and even more preferably 2.5 to 3.

Besides, the conditioning composition may comprise further ingredients conventionally used in the field of cosmetics, such as preservatives, chelating agents, stabilizers, oxidation inhibitors, plant extracts, ultraviolet absorbers, vitamins, dyes, and fragrances.

Cationic Polymers

A cationic polymer is a polymer having a cationic group or a group capable of being ionized into a cationic group, and in general, an amphoteric polymer acquiring net cationic charge is also included in the terminology. That is, the cationic polymer is a polymer containing an amino group or an ammonium group in a side chain of the polymer chain, or a polymer including a diallyl quaternary ammonium salt as a constituent unit, and examples thereof include cationized cellulose, cationic starch, cationic guar gum, a polymer or copolymer of a diallyl quaternary ammonium salt, and quaternized polyvinylpyrrolidone. Among these, from the viewpoint of softness, smoothness and easy finger-combing during shampooing, and easy manageability and moisture retention during drying, and from the viewpoint of stability of the agent, a polymer including a diallyl quaternary ammonium salt as a constituent unit, quaternized polyvinylpyrrolidone, and cationized cellulose are preferred, and a polymer or copolymer of a diallyl quaternary ammonium salt, and cationized cellulose are more preferred.

Specific examples of the polymer or copolymer of a diallyl quaternary ammonium salt include dimethyldiallylammonium chloride polymer (polyquaternium-6, for example, MERQUAT 100; Nalco Company), dimethyldiallylammonium chloride/acrylic acid copolymer (polyquaternium-22, for example, MERQUAT 280, MERQUAT 295; Nalco Company), and dimethyldiallylammonium chloride/acrylic acid amide copolymer (polyquaternium-7, for example, MERQUAT 550; Nalco Company).

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium 11, for example, GAFQUAT 734, GAFQUAT 755 and GAFQUAT 755N (all by ISP Japan, Ltd.)).

Specific examples of the cationized cellulose include a polymer of a quaternary ammonium salt obtained by adding glycidyl rimethylammonium chloride to hydroxyethylcellulose (polyquaternium-10, for example, RHEOGUARD G and RHEOGUARD GP (all by Lion Corp.), POLYMER JR-125, POLYMER JR-400, POLYMER JR-30M, POLYMER LR-400 and POLYMER LR-30M (all by Amerchol Corp.)), and a hydroxyethylcellulose/dimethyldiallylammonium chloride copolymer (polyquaternium-4, for example, CELQUAT H-100, CELQUAT L-200 (all by National Starch and Chemical Company)).

The cationic polymer may be used in combination of two or more kinds. Furthermore, the cationic polymer gives better effects when the content is increased, but an excessively high content of the cationic polymer may cause stability failure and a decrease in the viscosity of the agent alone or during mixing. From this viewpoint, and from the viewpoint of enhancing the feel to the touch, the content of the cationic polymer is preferably 0.001 to 20 wt %, more preferably 0.01 to 10 wt. %, and even more preferably 0.05 to 5 wt. %, based on the weight of the conditioning composition.

Silicones

In order to improve the feel of use, the conditioner preferably contains a silicone. Examples of the silicone include dimethylpolysiloxane, and modified silicone (for example, amino-modified silicone, fluorine-modified silicone, alcohol-modified silicone, polyether-modified silicone, epoxy-modified silicone, or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF 6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

wherein R' represents a hydroxyl group, a hydrogen atom or $R^X$; $R^X$ represents a substituted or unsubstituted monovalent hydrocarbon group having 1 to 20 carbon atoms; D represents $R^X$, R"—(NHCH$_2$CH$_2$)$_m$NH$_2$, OR$^X$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-867S, and KF-8015 (all by Shin-Etsu Chemical Co., Ltd.); and amodimethicone emulsions such as SM8704C, SM8904, BY22-079, F2-4671, and FZ-4672 (all by Dow corning Toray Co., Ltd.).

The total content of these silicones in the compositions of the present invention is usually 0.1 to 20 wt. %, preferably 0.2% to 10 wt. % and more preferably 0.5 to 5 wt. %, based on the weight of the conditioning composition.

Oil Component

For improving the feel upon use, the conditioner also may include an organic conditioning oil. The organic conditioning oil that is suitably used as a conditioning component is preferably a low-viscosity and water-insoluble liquid, and is selected from a hydrocarbon oil having at least 10 carbon atoms, a polyolefin, a fatty acid ester, a fatty acid amide, a polyalkylene glycol, and mixtures thereof. The viscosity of such an organic conditioning oil as measured at 40° C. is preferably 1 to 200 mPa·s, more preferably 1 to 100 mPa·s, and even more preferably 2 to 50 mPa·s. For the determination of the viscosity, a capillary viscometer may be used.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil.

The organic conditioning oil may be used in combination of two or more kinds, and the total concentration is typically in the range of 0.1 to 20 wt. %, preferably 0.2 to 10 wt. %, more preferably 0.5 to 5 wt. %, based on the weight of the conditioning composition.

Alcohols

From the viewpoint of improving the sense of touch and stability, the conditioner may also contain a higher alcohol having 8 carbon atoms or more. Usually, the higher alcohol has 8 to 24 carbon atoms, and preferably 16 to 22 carbon atoms. Specific examples thereof include cetyl alcohol, stearyl alcohol, behenyl alcohol, and mixtures thereof.

The higher alcohol may be used in combination of two or more kinds, and the content thereof is typically 0.1 to 20 wt. %, preferably 0.2 to 10 wt. %, more preferably 0.5 to 5 wt. %, based on the weight of the conditioning composition.

Additionally polyols may suitably be comprised in the compositions. Examples of the polyalkylene glycol include polyethylene glycol and polypropylene glycol, and a mixture of the two may be used, or a copolymer of ethylene oxide and propylene oxide may also be used.

Cationic Surfactant

The conditioner may also contain a cationic surfactant. The cationic surfactant is preferably a mono-long chain alkyl quaternary ammonium salt, having a $C_8$-$C_{24}$ alkyl residue and three $C_1$-$C_4$ alkyl residues.

Preferably at least one mono alkyl quaternary ammonium surfactant is selected from the compounds with the general formula wherein $R_8$ is a saturated or unsaturated, branched or straight alkyl chain with 8-22 C atoms or wherein $R_{12}$ is a saturated or unsaturated, branched or straight alkyl chain with 7-21 C atoms and n is an integer of 1-4, or wherein $R_{12}$ is a saturated or unsaturated, branched or straight alkyl chain with 7-21 C atoms and n is an integer of 1-4, and $R_9$, $R_{10}$ and $R_{11}$ are independent from each other an alkyl group with 1 to 4 carbon atoms, hydroxyl alky chain with 1 to 4 carbon atoms, or ethoxy or propoxy group with a number of ethoxy or propoxy groups varying in the range of 1 to 4, and X is chloride, bromide, methosulfate or ethosulfate Suitable cationic surfactants are, for example, long-chain quaternary ammonium compounds which can be used alone or in admixture with one another, such as cetyl trimethyl ammonium chloride, myristyl trimethyl ammonium chloride, behentrimonium chloride, trimethyl cetyl ammonium bromide, stearyl trimethyl ammonium chloride, stearyl trimonium chloride and stearamidopropyltrimonium chloride.

The cationic surfactant may be used in combination of two or more kinds, and the content thereof is typically 0.1 to 20 wt. %, preferably 0.2 to 10 wt. %, more preferably 0.5 to 5 wt. %, based on the total weight of the conditioning composition.

4. Hair Treatment Process

In the method for reducing the frizziness and improving the manageability of hair according to the present invention, there are no particular limitations with respect to the treatment of the hair with the cleansing composition and/or the conditioning composition.

The hair cleansing composition of the present invention may be used like a conventional shampoo. It is typically applied to the hair at a ratio of hair to shampoo usually in the range of between 1:0.05 and 1:0.5 and massaged into the hair for a time of 1 to 5 minutes at a temperature between 20 and 40° C., before it is rinsed off with water. Then, the hair may be dried with a towel. In case it is not desired to subsequently apply a conditioner, e.g., the one of the present invention or a conventional one, the hair may then be allowed to dry, optionally using a hair dryer.

The conditioning composition of the present invention may be of the rinse-off type or the leave-in type, and can be used like a conventional hair conditioner. It is typically applied after shampooing with the shampoo of the present invention or a conventional shampoo.

The rinse-off type conditioner is usually applied to the still wet hair just after rinsing off the shampoo, but may also be applied to towel-dry hair. The leave-in to conditioner is typically applied to the towel-dry hair. In both cases, the conditioner is used at a ratio of hair to conditioner in the range of usually between 1:0.05 and 1:1 and massaged into the hair for a time of usually 1 to 15 minutes at a temperature between 20 and 40° C. A rinse-off type conditioner is then rinsed off the hair with water.

The conditions for the hair drying after using the shampoo or the conditioner are not particularly limited. The hair may either be allowed to dry at ambient temperature, or a hair dryer may be used, typically at a temperature of the hot air stream of 60 to 140° C., preferably 60 to 100° C. The temperature refers to the temperature of the air stream on the hair. Suitably, the temperature can be determined in a contact-less thermal radiation measurement, e.g., by capturing the area where the hot air stream comes into contact with the hair with a thermal radiation detector such as an infrared thermometer.

In order to enhance the straightening and frizz reducing effect, it is preferable to perform the drying with a hair dryer under continuous combing and/or with the hair being held in an elongated state using a brush or the like, for a time period of usually within the range of 1 to 15 minutes, depending on the amount and length of the hair.

It is possible to use only the shampoo or only the conditioner of the present invention, e.g., in combination with a conventional conditioner and shampoo, respectively. For enhancing the frizz reducing effect, however, it is preferable to use the shampoo and the conditioner of the present invention in combination.

For achieving the frizz reducing and manageability improving effect of the invention, the shampoo and/or the conditioner should preferably be used repeatedly. Carrying out the treatment repeatedly means that the treatment is carried out more than once. Typically, the treatment is carried out at least once a week, preferably at least twice a week, more preferably at least three times a week, yet more preferably every day, until the desired effect is achieved. For instance, the treatment may be performed by using the cleansing composition and the conditioning composition as the shampoo and conditioner for everyday hair care.

If the treatment with both the cleansing composition and the conditioning composition is performed every day, then the frizz reducing effect of the present invention may be readily observable after the second or third application already. It may take longer until the effects are clearly recognized if only one of the shampoo and the conditioner is used, or if the shampoo and/or the conditioner are used at a less frequent interval, possibly alternating with the usage of a conventional shampoo or conditioner.

EXAMPLES

The present invention is now illustrated by the following non-limiting examples.

Example 1

Shampoo (Cleansing Composition)

|  | Inventive | Comparative |
| --- | --- | --- |
| Sodium laureth sulphate | 10.0 | 10.0 |
| Cocamidopropyl betaine | 3.0 | 3.0 |
| Sodium lauroyl glutamate | 1.0 | 1.0 |
| Cocoglucoside | 1.0 | 1.0 |
| Glyceryl oleate | 1.0 | 1.0 |
| PEG-18 Glyceryl oleate/cocoate | 0.5 | 0.5 |
| Lactic acid | — | 0.6 |
| Glyoxylic acid | 0.5 | — |
| Fragrance | 0.5 | 0.5 |
| Preservative | 0.5 | 0.5 |
| Water | q.s. to 100 | q.s. to 100 |
| pH | 2.8 | 2.8 |

Conditioner (Conditioning Composition)

|  | Inventive | Comparative |
| --- | --- | --- |
| Cetearyl alcohol | 4.0 | 4.0 |
| Cetrimonium chloride | 1.0 | 1.0 |
| Dimethicone | 1.0 | 1.0 |
| Glycerine | 0.5 | 0.5 |
| Lactic acid | — | 0.6 |
| Glyoxylic acid | 0.5 | — |
| Fragrance | 0.5 | 0.5 |
| Preservative | 0.5 | 0.5 |
| Water | to 100 | to 100 |
| pH | 2.5 | 2.5 |

The amounts are indicated as weight percentage. In the composition according to the invention and the comparative composition, respectively, the content of glyoxylic acid and lactic acid was selected such that the molar concentration is the same.

Test and Evaluation

Figure 1:
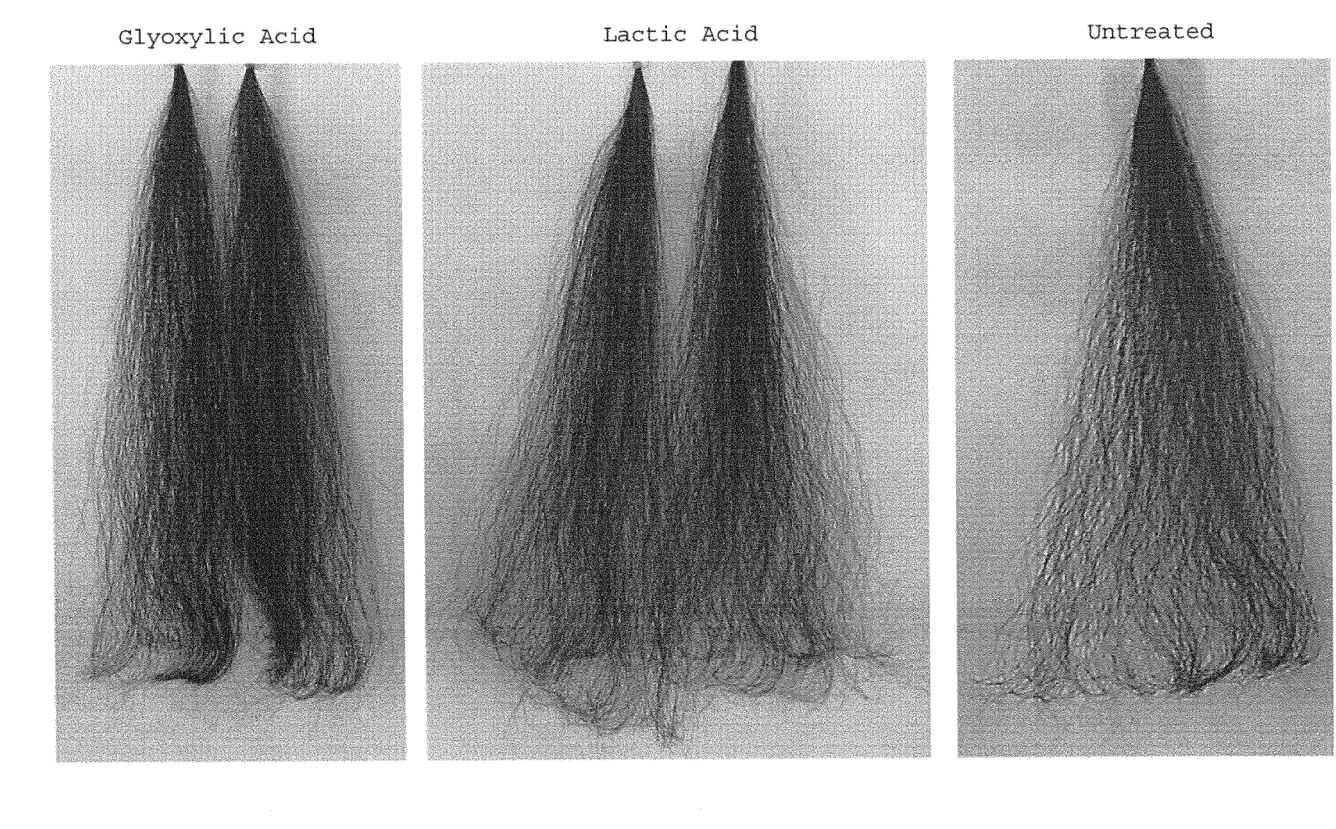
FIG. 1: Photographs of the hair samples of the Test Example. The samples in the leftmost photograph and in the middle photograph were subjected to three treatment cycles with the cleansing and the conditioning compositions of the present invention and with the reference compositions, respectively. The sample in the rightmost photograph is an untreated sample.

Samples of frizzy hair (bundles of Indian frizz hair, untreated, obtained from IHIP, International Hair Importers & Products, NY; see rightmost photograph in FIG. 1) were treated with the above-described composition according to the invention and the comparative composition, respectively.

First, the samples where shampooed by applying the above-described cleansing composition of the invention and the comparative cleansing composition (two samples for each composition) to the hair at a ratio of hair to shampoo of 1:0.2. The shampoo was massaged into the hair for 2 minutes and rinsed off with water. Then, the samples were dried with a towel.

The above-described conditioning composition of the present invention was then applied to the samples shampooed with the cleansing composition of the invention, while the comparative conditioner was applied to the samples shampooed with the comparative cleansing composition. The conditioners were applied at a ratio of hair to conditioner of 1:0.5 and left on the hair for 15 minutes. Then, the hair was dried under continuous combing using a blow dryer at a temperature of about 80° C. The temperature was measured by holding an infrared thermometer at a distance of about 20 to 40 cm from the hair and scanning the area where the air stream comes into contact with the hair. The average of at least ten readings is then taken as the temperature.

After 24 hours, the thus treated samples were rinsed with water, and the above-described steps of shampooing and conditioning were repeated in the second and further treatment cycles.

FIG. 1 shows the result after three of these treatment cycles. The photographs were taken immediately before the rinsing with water and the beginning of the next treatment cycle. The left-hand photograph shows the sample treated with the shampoo and conditioner of the present invention, while the photograph in the middle shows the sample treated with the comparative compositions As apparent from the figure, the frizziness of the samples treated with the inventive composition is reduced remarkably, in comparison with the comparative samples and the untreated reference sample in the right-hand photograph. For the comparative samples, on the other hand, the frizziness is almost the same as for the untreated sample. As a result, it was found that the process according to the present invention provides a remarkable improvement of manageability and a reduction of frizziness.

Example 2: Cleansing Composition

|  | % by weight |
| --- | --- |
| Sodium laureth sulphate | 10.0 |
| Cocoyl betaine | 3.0 |
| Sodium lauryl ether carboxylate | 2.0 |
| Decyl glucoside | 4.0 |
| Polyquaternium-7 | 0.5 |
| Glyoxylic acid | 1.0 |
| Sodium chloride | 1.0 |
| Fragrance | 0.7 |
| Preservative | 0.5 |
| Water | q.s. to 100 |

The pH of the composition is 2.6.

Example 3: Cleansing Composition

|  | % by weight |
| --- | --- |
| Sodium laureth sulphate | 8.0 |
| Cocamidopropyl betaine | 4.0 |
| Sodium lauryl ether carboxylate | 3.0 |
| Decyl glucoside | 5.0 |
| Polyquaternium-7 | 0.5 |
| Dimethicone | 0.2 |
| Glyoxylic acid | 0.5 |
| Glycol distearate | 2.0 |
| Panthenol | 0.5 |
| Sodium chloride | 1.0 |
| Fragrance | 0.7 |
| Preservative | 0.5 |
| Water | q.s. to 100 |

The pH of the composition is 2.7.

Example 4: Cleansing Composition

|  | % by weight |
| --- | --- |
| Sodium laureth sulphate | 8.0 |
| Lauryl betaine | 4.0 |
| Plantaren PS 300 | 9.5 |
| Glyceryl laurate | 1.0 |
| Polyquaternium-10 | 0.5 |
| Dimethicone | 0.2 |
| Glyoxylic acid | 0.75 |
| Glycol distearate | 2.0 |
| Glycerin | 0.5 |
| Sodium chloride | 0.9 |
| Fragrance | 0.5 |
| Preservative | 0.5 |
| Water | q.s. to 100 |

The pH of the composition is 2.9.

Example 5: Cleansing Composition

|  | % by weight |
| --- | --- |
| Sodium laureth sulphate | 9.0 |
| Lauryl betaine | 4.0 |
| Sodium lauroyl glutamate | 1.0 |
| Plantaren PS 300 | 9.5 |
| Glyceryl laurate | 1.0 |
| Polyquaternium-10 | 0.5 |
| Dimethicone | 0.8 |
| Amodimethicone | 0.2 |
| Glyoxylic acid | 0.75 |
| Glycol distearate | 2.0 |
| Glycerin | 0.5 |
| PEG-18 Glyceryl oleate/cocoate | 0.8 |
| Fragrance | 0.5 |
| Preservative | 0.5 |
| Water | q.s. to 100 |

The pH of the composition is 2.9.

Example 6: Conditioning Composition (Rinse-Off)

|  | % by weight |
| --- | --- |
| Cetearyl alcohol | 5.0 |
| Behentrimonium chloride | 0.8 |
| Guarhydroxypropyltrimonium chloride | 0.3 |
| Quaternium-80 | 0.2 |
| Panthenol | 0.5 |
| Glyoxylic acid | 0.5 |
| Fragrance | 0.7 |
| Preservative | 0.5 |
| Water | q.s. to 100 |

The pH of the composition is 2.9.

Example 7: Conditioning Composition (Rinse-Off)

|  | % by weight |
| --- | --- |
| Cetearyl alcohol | 5.0 |
| Behenamidopropyldimethyl amine | 0.8 |
| Ceteareth-20 | 0.8 |
| Dimethicone | 0.2 |
| Isopropyl myristate | 0.2 |
| Almond oil | 0.2 |
| Panthenol | 0.5 |
| Glyoxylic acid | 1.0 |
| Polyquaternium-37 | 0.8 |
| Fragrance | 0.7 |
| Preservative | 0.5 |
| Water | q.s. to 100 |

The pH of the composition is 2.6.

Example 8: Conditioning Composition (Leave-In)

|  | % by weight |
| --- | --- |
| Ethanol | 20.0 |
| Cetrimonium chloride | 0.8 |
| Quaternium-80 | 1.0 |
| Almond oil | 0.2 |
| PEG-40 Hydrogenated castor oil | 0.8 |
| Glycerin | 0.5 |
| 1,2-Propylene glycol | 10.0 |
| Glyoxylic acid | 0.5 |
| Fragrance, preservative | q.s. |
| Water | q.s. to 100 |

The pH of the composition is 2.5.

Example 9: Conditioning Composition (Leave-In)

|  | % by weight |
| --- | --- |
| Ethanol | 20.0 |
| Behentrimonium chloride | 0.8 |
| Dimethicone copolyol | 0.2 |
| Argan oil | 0.2 |
| PEG-40 Hydrogenated castor oil | 0.8 |
| Panthenol | 0.5 |
| 1,2-Propylene glycol | 10.0 |
| Glyoxylic acid | 0.5 |
| Fragrance, preservative | q.s. |
| Water | q.s. to 100 |

The pH of the composition is 2.5.

The invention claimed is:

1. Process for reducing the frizziness and improving the manageability of hair, comprising the treatment of the hair with:
  a hair cleansing composition having a pH of 2 to 3.5 and comprising an anionic surfactant and glyoxylic acid; and
  a hair conditioning composition having a pH of 2 to 3.5 and comprising a cationic surfactant and glyoxylic acid
  wherein the cleansing composition and the conditioning composition comprise the glyoxylic acid at a concentration in the range of 0.1 to 5% by weight, and wherein the hair is treated with the cleansing composition and directly afterwards treated with the conditioning composition
  wherein the hair is dried at 60 to 140° C. under blowing, after the conditioning composition has been rinsed off from the hair, with a blow dryer.

2. The process according to claim 1, wherein in the cleansing composition the anionic surfactant is selected from alkyl sulphates or ether sulphates.

3. The process according to claim 1, wherein the cleansing composition has an anionic surfactant concentration of 5 to 50 wt. % based on the weight of the cleansing composition.

4. The process according to claim 1, wherein the cleansing composition further comprises a conditioning component selected from the group consisting of a cationic polymer and silicone.

5. The process according to claim 1, wherein the conditioning composition further comprises one or more higher alcohols having 8-24 carbon atoms.

6. The process according to claim 1, wherein the conditioning composition is not rinsed off from the hair after application.

7. The process according to claim 1, wherein the cleansing composition and conditioning composition are rinsed off from the hair after application.

8. The process according to claim 1, wherein the cleansing composition and the conditioning composition are applied repeatedly at least once a week.

* * * * *